United States Patent [19]

Mayer

[11] Patent Number: 4,895,028

[45] Date of Patent: Jan. 23, 1990

[54] METHOD OF PULL-TESTING WIRE CONNECTORS ON AN ELECTRICAL DEVICE

[75] Inventor: Robert T. Mayer, Rye, N.Y.

[73] Assignee: U.S. Philips Corporation, New York, N.Y.

[21] Appl. No.: 303,522

[22] Filed: Jan. 27, 1989

[51] Int. Cl.[4] ............................................. G01N 3/08
[52] U.S. Cl. .................................... 73/827; 73/862.39
[58] Field of Search ..................... 73/827, 862.39, 842

[56] References Cited

U.S. PATENT DOCUMENTS 3,572,108  3/1971  McShane et al. ..................... 73/827

Primary Examiner—Jerry W. Myracle
Attorney, Agent, or Firm—Robert T. Mayer

[57] ABSTRACT

In pull-testing wire bonds on an electrical device, an upward pulling force is applied to a wire loop by a motor-driven loading arm through a hook which is connected to the free end of a flexible cantilever beam in the arm. A strain gauge is provided on the beam to measure its deflection and thus the applied pulling force and supply a signal corresponding to this measured force. The actual forces applied to the bonds is calculated by generating a signal signifying the distance the hook has moved when the strain gauge starts to generate a signal.

4 Claims, 1 Drawing Sheet

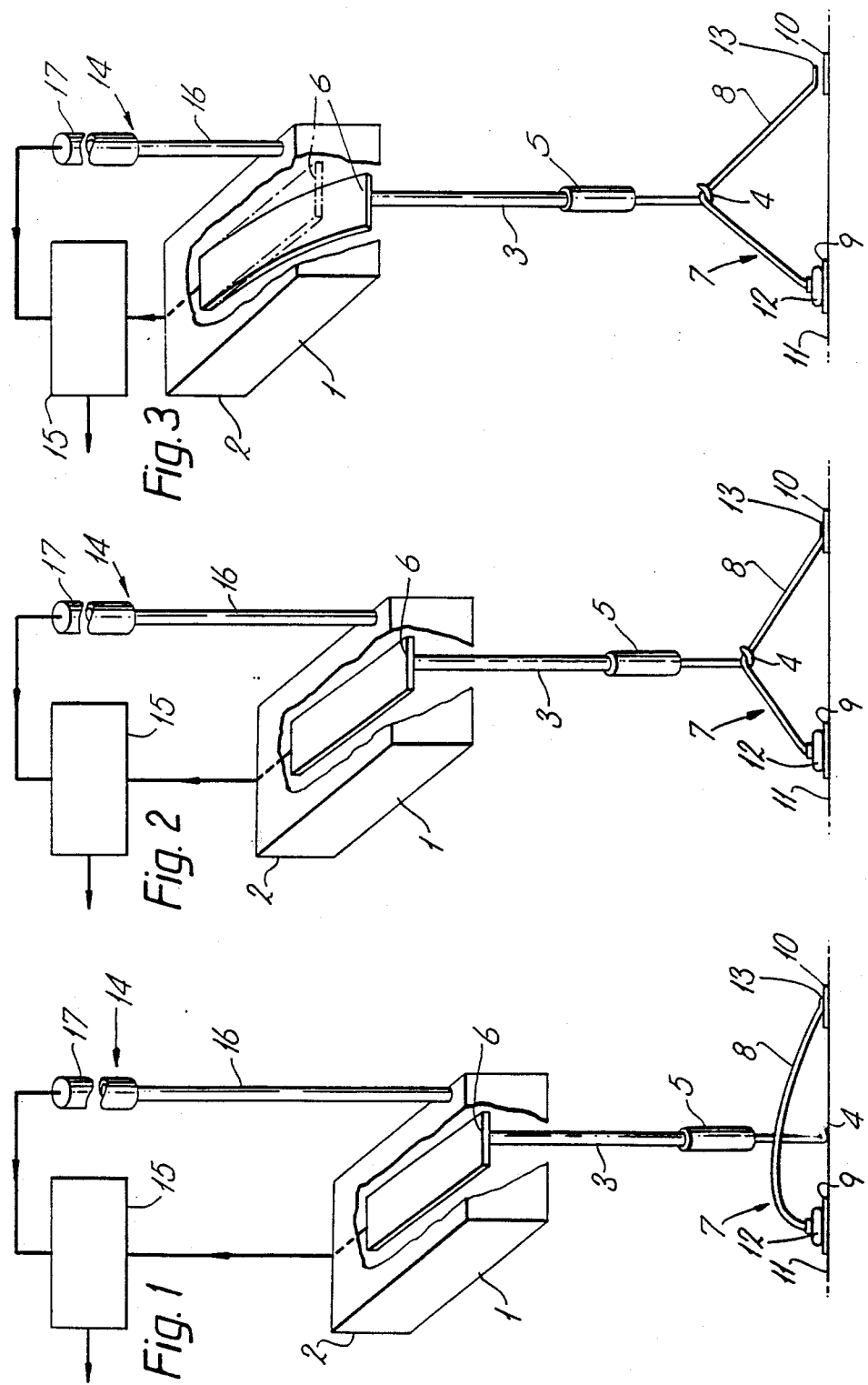

METHOD OF PULL-TESTING WIRE CONNECTORS ON AN ELECTRICAL DEVICE

The invention relates to a method of pull-testing wire connectors on an electrical device such as an integrated circuit. Such connectors consist of an electrically conductive wire which extends between and is bonded at its ends to two bonding pads on the electrical device by, for example, ultrasonic welding. The wire forms a loop between the pads which may be, two dies or a terminal and a die.

There is a standard method of pull-testing a wire connector in which a pulling force is applied to the wire loop at a point intermediate the ends of the loop in a direction away from the plane containing the bonds until the wire connector breaks, usually by failure of one of the bonds, or is stressed to a predetermined value. The force is applied by means of a device which moves first to tauten the wire loop and then to apply the pulling force to the loop. The device comprises means such as a force transducer for measuring the applied force and supplying a signal corresponding to the measured force.

An improved method of this type is disclosed in pending U.S. patent application Ser. No. 089,378 filed Aug. 26, 1987 which is incorporated by reference herein and is assigned to the assignee of this application.

That improved method takes into account that the actual forces applied to wire bonds in the testing procedure vary depending on the length of the wire loop between the bonds.

Two variations of the improved method are disclosed in that application. One variation measures the total distance a force applying device moves to stress a wire loop in a prescribed manner and also measures the movement of a strain transducer relative to the force applying device as the prescribed stress is applied. From these measurements the actual forces applied to bonds at the ends of a wire loop are calculated.

The other variation measures the height of the tautened loop before stress is applied and uses that height in conjunction with the relative movement of the strain transducer as the prescribed stress is applied to calculate the actual forces applied to the bonds.

It is an object of this invention to provide an alternative method of pull-testing wire bonds in which variations in loop height due to variations in the length of the loop are also taken into account.

According to the invention there is provided a method of pull-testing wire bonds at the ends of a wire loop on an electrical device in which at least one of the bonds is located in a predetermined plane. The method includes applying a force to the wire loop by a device which moves away from the predetermined plane first to tauten the loop and then to apply a pulling force to the loop. The pulling force is measured and a signal is generated signifying the measured pulling force. A signal is also generated indicating when the pulling force starts to be applied and in response thereto a signal is generated signifying the distance the force applying device has moved to tauten the loop. The distance signal and the signal signifying the measured pulling force are both supplied to a calculating device which calculates a corrected pulling force in accordance with variations in the distance the force applying device has had to move to tauten the loop.

The invention also provides an apparatus for carrying out the method. The apparatus comprises a device which is movable first to tauten a wire loop and then to apply a pulling force to the loop. Also included are means for measuring the applied pulling force and supplying a signal corresponding to the measured force. In addition there are means for measuring the movement of the force applying device and for supplying a signal which corresponds to the distance through which the force-applying device has moved when the pulling force begins to be applied. A calculating device into which these two signals are fed calculates the actual forces applied to the bonds at the ends of the wire loop.

A preferred embodiment of the apparatus according to the invention includes means for measuring the applied pulling force. This comprises a force transducer and means for measuring the movement of the force applying device. This latter means comprises a displacement transducer which is arranged to measure and to supply a signal corresponding to the distance through which the force-applying device moves to tauten the wire loop. The signals from the two transducers are fed to the calculating device and the latter is programmed to calculate the actual forces applied to the wire bonds at the ends of the loop.

The force applying device comprises a member movable by means of a motor and a hook which is engageable with the wire loop. The hook is connected to the movable member by means of the force transducer first to engage and tauten the loop and then to apply the pulling force thereto. The force transducer comprises an element which is connected to the movable member. It is flexible under load for movement relative to the movable member. A strain gauge is provided for measuring the deflection of the flexible element and for supplying to the calculating device a signal corresponding to the measured deflection. The hook is connected to the flexible part of the element. The displacement transducer is arranged to measure and to supply to the calculating device a signal corresponding to the distance through which the movable member moves to tauten the wire loop, that is, the distance it has moved when the strain gauge begins to supply a signal. The calculating device calculates the actual forces applied to wire bonds from the two signals applied to it.

An example of the method according to the invention, and an embodiment of the apparatus according to the invention for carrying out the method, will now be described with reference to the accompanying drawing, in which:

FIG. 1 is a schematic perspective view of an apparatus according to the invention at the beginning of a test of the method according to the invention, FIG. 2 is a view similar to FIG. 1 showing the force applying device at the end of its initial movement to tauten the loop of a wire connector, and FIG. 3 is a view similar to FIGS. 1 and 2 showing the force applying device at the point at which one of the bonds at the ends of the wire has parted.

The apparatus shown in FIGS. 1, 2 and 3 comprises a substantially horizontal loading arm 1 which is pivotally supported at one end 2 for movement in upward and downward directions by means of a motorized drive (not shown). Rod 3 depends vertically from the other end of the loading arm which end is free to move. At its lower end rod 3 carries hook 4. The hook is connected to the rod by an adjustable coupling 5 which permits adjustment of the hook relative to the rod in the axial direction of the rod. At its upper end rod 3 is connected to the free end of flexible cantilever beam 6 located inside arm 1. A strain gauge (not shown) is provided on beam 6 to measure its deflection. Beam 6 and the gauge together form a known type of force transducer.

The apparatus thus far described is known and operates in the following manner. Assume bonds 12 and 13 of connector 7 are to be tested. Connector 7 includes wire 8 bonded at its ends to die pads 9 and 10 on substrate 11 by ball bond 12 and wedge bond 13, respectively. With loading arm 1 in the lowered position shown in FIG. 1, hook 4 rests on the upper surface of substrate 11 which provides a reference plane. Hook 4 lies directly below the center of wire loop 8. The arm 1 is then raised to bring hook 4 into engagement with the wire loop and then to tauten the loop, as shown in FIG. 2. Further upward movement of loading arm 1 stresses the wire, with a corresponding deflection of beam 6 in the arm until a predetermined stress value is reached or the wire bond breaks either by parting of the wire or, as shown in FIG. 3, by failure of the weaker of the two bonds 12 or 13. Since the load/deflection characteristics of beam 6 are known, a measurement of the pulling force applied to the wire loop by arm 1 is obtained from the strain gauge which measures the deflection of beam 6.

The forces applied to bonds 12 and 13 will vary with the length of the wire loop. The length of the loop is a factor determining the height of the loop when tautened and this is an element in determining the forces in the wire at the bonds. To ascertain the height of the tautened loop the upward movement of loading arm 1 during each test is measured with displacement transducer 14. Transducer 14 feeds a signal indicative of this movement to calculating device 15 which comprises a computer.

Also fed to calculating device 15 is the signal from the applied pulling force transducer formed by beam 6 and its associated strain gauge. Calculating device 15 determines the measured force applied to the wire loop by loading arm 1 in accordance with variations in the loop height from a given value to obtain a corrected measurement of the forces actually applied to bonds 12 and 13. Displacement transducer 14 measures the distance through which arm 1 moves from the starting position with hook 4 on the plane provided by the surface of substrate 11 (FIG. 1) to the moment at which the strain transducer starts to generate a signal indicating the application of force to wire 8. At that time in response to the initiation of the signal from the strain gauge, a signal from displacement transducer 14 indicating the distance arm 1 has moved to tauten the loop is supplied to calculating device 15.

It is to be understood that under ideal conditions, that is, with the length of the wire loop being exactly the desired length and with hook 4 being located at the middle of the loop the height of the tautened loop can be ascertained. Consequently, the angle wire 8 presents to the horizontal and vertical when tautened can also be ascertained. With this information through resolution the forces applied to bonds 12 and 13 can be calculated.

With the information regarding the height of a wire loop under ideal conditions and the information concerning the distance arm 1 has moved to have the strain gauge begin to produce a signal, the angle of wire 8 to the horizontal and vertical when tautened can be determined for all tests. Consequently, the actual forces applied to bonds 12 and 13 in any test can be calculated in calculating device 15 through resolution.

It is also to be understood that the reference plane could be the plane containing bonds 12 and 13, which in the example shown are at the same level. More conveniently, as shown in FIG. 1, the upper surface of substrate 11 is utilized as the reference plane. Consequently, after each test loading arm 1 can simply be lowered until hook 4 abuts substrate 11 to determine the starting position of the arm for the next test. The computer can also be programmed to make allowance in the measurement of the loop height for the cross-sectional diameter of the wire of which hook 4 is made.

Displacement transducer 14 may be of any convenient known form. In the embodiment shown it consists of a linear variable differential transformer comprising a stationary coil (not shown) arranged within a protective magnetic shield in a fixed, vertically disposed sleeve 17 and comprising a primary winding between two secondary windings which are wired in series opposition. The armature (not shown) of the transformer is carried on a vertically arranged rod 16 which is connected at its lower end to loading arm 1 at or near the free end thereof for movement up and down with the arm. The armature moves within the hollow core of the coil and, when the primary winding is energized, induces a voltage from the primary to the secondary windings. The position of the armature within the coil determines the level of the voltage at each secondary winding and hence an output voltage that is proportional to the displacement of the armature from null, i.e., the midway position.

It should be apparent that various modifications of the above will be evident to those skilled in the art and that what is disclosed herein is for illustrative purposes and is not to be considered restrictive.

What is claimed is:

1. A method of pull-testing wire bonds at the ends of a wire loop on an electrical device in which at least one of the bonds is located in a predetermined plane, said method including applying a force to said wire loop by a device which moves away from said plane first to tauten said loop and then to apply a pulling force to said loop, measuring the pulling force and generating a signal signifying the measured pulling force, generating a signal indicating when said pulling force starts to apply stress to said wire loop and in response thereto generating a signal signifying the distance said force applying device has moved to tauten said loop, and supplying said distance signal and said signal signifying the measured pulling force to a calculating device which calculates the actual pulling forces applied to said bonds in accordance with variations in the distance the force applying device has had to move to tauten said loop.

2. An apparatus for carrying out the method claimed in claim 1, comprising a force applying device which is movable first to tauten a wire loop and then to apply a pulling force to the loop, means for measuring the applied pulling force and for supplying a signal corresponding to the measured force, means for measuring the distance the force applying device has moved at the time the force measuring means starts to produce a signal and for supplying a signal which corresponds to the distance through which the force applying device has moved at that time and a calculating device into which the applied pulling force signal and the distance signal can be fed and which is programmed to calculate the actual force applied to said wire bonds in accordance with variation in the distance through which the force applying device moves to tauten the wire loop.

3. An apparatus as claimed in claim 2, wherein the means for measuring the applied force comprises a force transducer and the means for measuring the movement of the force applying device comprises a displacement transducer.

4. An apparatus as claimed in claim 3, in which the force applying device comprises a member movable by means of a motor and a hook which is engageable with the wire loop in the operation of the apparatus and which is connected to said movable member, said applied pulling force measuring means including a force transducer for movement with said movable member first to engage and tauten the loop and then to apply the pulling force thereto, said force transducer comprising a cantilever beam which is connected to said movable member for movement therewith and which is flexible under load for movement relative to said movable member and a strain gauge for measuring the deflection of said cantilever beam and for supplying to the calculating device a signal corresponding to the measured deflection, said hook being connected to the flexible part of said cantilever beam.

* * * * *